(12) United States Patent
Zhang et al.

(10) Patent No.: US 8,494,618 B2
(45) Date of Patent: Jul. 23, 2013

(54) INTRACARDIAC IMPEDANCE AND ITS APPLICATIONS

(75) Inventors: Yunlong Zhang, Mounds View, MN (US); James O. Gilkerson, Stillwater, MN (US); Yongxing Zhang, Maple Grove, MN (US); Boyce Moon, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2284 days.

(21) Appl. No.: 11/208,922

(22) Filed: Aug. 22, 2005

(65) Prior Publication Data
US 2007/0043394 A1     Feb. 22, 2007

(51) Int. Cl.
*A61B 5/04*     (2006.01)
*A61N 1/00*     (2006.01)

(52) U.S. Cl.
USPC ............................... 600/509; 600/515; 607/18

(58) Field of Classification Search
USPC ..................................... 600/509, 515; 607/18
See application file for complete search history.

(56) References Cited

U.S. PATENT DOCUMENTS

| | | | | |
|---|---|---|---|---|
| 5,179,946 | A | * | 1/1993 | Weiss .................................. 607/4 |
| 5,188,106 | A | * | 2/1993 | Nappholz et al. ................ 607/24 |
| 5,318,597 | A | | 6/1994 | Hauck et al. |
| 5,626,623 | A | | 5/1997 | Kieval et al. |
| 5,788,643 | A | | 8/1998 | Feldman |
| 5,861,008 | A | * | 1/1999 | Obel et al. ....................... 607/11 |
| 6,070,100 | A | | 5/2000 | Bakels et al. |
| 6,076,015 | A | | 6/2000 | Hartley et al. |
| 6,219,579 | B1 | | 4/2001 | Bakels et al. |
| 6,223,079 | B1 | | 4/2001 | Bakels et al. |
| 6,223,082 | B1 | | 4/2001 | Bakels et al. |
| 6,238,420 | B1 | | 5/2001 | Bakels et al. |
| 6,266,554 | B1 | | 7/2001 | Hsu et al. |
| 6,275,732 | B1 | | 8/2001 | Hsu et al. |
| 6,278,894 | B1 | | 8/2001 | Salo et al. |
| 6,280,389 | B1 | | 8/2001 | Ding et al. |
| 6,308,095 | B1 | | 10/2001 | Hsu et al. |
| 6,438,410 | B2 | | 8/2002 | Hsu et al. |
| 6,449,503 | B1 | | 9/2002 | Hsu |
| 6,491,639 | B1 | * | 12/2002 | Turcott ......................... 600/508 |
| 6,522,914 | B1 | * | 2/2003 | Huvelle et al. ................. 600/509 |
| 6,556,866 | B2 | | 4/2003 | Dal Molin et al. |
| 6,751,503 | B1 | | 6/2004 | Kroll |

(Continued)

OTHER PUBLICATIONS

"U.S. Appl. No. 11/136,894, Final Office Action mailed Oct. 18, 2007", 9 pgs.

(Continued)

*Primary Examiner* — Nicole F Lavert
(74) *Attorney, Agent, or Firm* — Schwegman Lundberg & Woessner, P.A.

(57) ABSTRACT

A system to measure intracardiac impedance includes implantable electrodes and a medical device. The electrodes sense electrical signals of a heart of a subject. The medical device includes a cardiac signal sensing circuit coupled to the implantable electrodes, an impedance measurement circuit coupled to the same or different implantable electrodes, and a controller circuit coupled to the cardiac signal sensing circuit and the impedance measurement circuit. The cardiac signal sensing circuit provides a sensed cardiac signal. The impedance measurement circuit senses intracardiac impedance between the electrodes to obtain an intracardiac impedance signal. The controller circuit determines cardiac cycles of the subject using the sensed cardiac signal, and detects tachyarrhythmia using cardiac-cycle to cardiac-cycle changes in a plurality of intracardiac impedance parameters obtained from the intracardiac impedance signal.

28 Claims, 11 Drawing Sheets

U.S. PATENT DOCUMENTS

| | | | |
|---|---|---|---|
| 6,751,504 B2 | 6/2004 | Fishler | |
| 6,754,530 B2 | 6/2004 | Bakels et al. | |
| 7,283,873 B1 | 10/2007 | Park et al. | |
| 2002/0002389 A1* | 1/2002 | Bradley et al. | 607/8 |
| 2003/0100925 A1* | 5/2003 | Pape et al. | 607/17 |
| 2003/0114889 A1* | 6/2003 | Huvelle et al. | 607/17 |
| 2003/0204212 A1 | 10/2003 | Burnes et al. | |
| 2003/0216657 A1 | 11/2003 | Holmstrom et al. | |
| 2004/0015081 A1 | 1/2004 | Kramer et al. | |
| 2004/0015196 A1 | 1/2004 | Holmstrom et al. | |
| 2004/0049235 A1* | 3/2004 | Deno et al. | 607/9 |
| 2004/0049238 A1 | 3/2004 | Jarverud | |
| 2004/0078058 A1 | 4/2004 | Holmstrom et al. | |
| 2004/0267142 A1* | 12/2004 | Paul | 600/509 |
| 2005/0038481 A1 | 2/2005 | Chinchoy et al. | |
| 2005/0043895 A1* | 2/2005 | Schechter | 702/19 |
| 2005/0049646 A1 | 3/2005 | Czygan et al. | |
| 2005/0085734 A1* | 4/2005 | Tehrani | 600/484 |
| 2005/0124901 A1* | 6/2005 | Misczynski et al. | 600/509 |
| 2005/0182447 A1* | 8/2005 | Schecter | 607/2 |
| 2005/0215914 A1* | 9/2005 | Bornzin et al. | 600/508 |
| 2005/0216067 A1* | 9/2005 | Min et al. | 607/17 |
| 2005/0277992 A1* | 12/2005 | Koh et al. | 607/9 |
| 2005/0288725 A1* | 12/2005 | Hettrick et al. | 607/17 |
| 2006/0020218 A1* | 1/2006 | Freeman et al. | 600/509 |
| 2006/0241512 A1 | 10/2006 | Kwok et al. | |
| 2006/0271119 A1 | 11/2006 | Ni et al. | |
| 2006/0271121 A1 | 11/2006 | Ding et al. | |
| 2007/0066905 A1* | 3/2007 | Zhang | 600/509 |
| 2007/0100246 A1* | 5/2007 | Hyde | 600/509 |
| 2007/0129639 A1* | 6/2007 | Zhang et al. | 600/509 |
| 2007/0149890 A1* | 6/2007 | Li et al. | 600/515 |
| 2007/0239044 A1* | 10/2007 | Ghanem et al. | 600/509 |
| 2008/0114410 A1 | 5/2008 | Ding et al. | |

OTHER PUBLICATIONS

"U.S. Appl. No. 11/136,894, Response filed Jul. 26, 2007 to Non-Final Office Action mailed Apr. 26, 2007", 15 pgs.

"U.S. Appl. No. 11/264,941, Response filed Jan. 24, 2008 to Final Office Action mailed Sep. 24, 2007", 15 pgs.

"U.S. Appl. No. 11/264,941, Response filed Nov. 26, 2007 to Final Office Action mailed Sep. 24, 2007", 16 pgs.

"U.S. Appl. No. 11/264,941, Final Office Action Mailed Sep. 24, 2007", 8 pgs.

"Non-Final Office Action mailed Apr. 10, 2007 in U.S. Appl. No. 11/264,941", 11 pgs.

"Non-Final Office Action mailed Apr. 26, 2007 in U.S. Appl. No. 11/136,894", 11 Pages.

"Response filed Jul. 10, 2007 to Non-Final Office Action mailed Apr. 10, 2007 in U.S. Appl. No. 11/264,941", 16 pgs.

Abe, H., et al., "Asynchronous Relaxation of the Ischemic Left Ventricle", *Japanese Circulation Journal*, 46(1), (1982), 103-112.

Yinghong, Yu, et al., "A Cardiac Resynchronization System Employing Mechanical Measurement of Cardiac Walls", U.S. Appl. No. 11/549,676, filed Oct. 16, 2006, 28 Pages.

Yu, Yinghong, et al., "Biventricular mechnical asynchrony predicts hemodynamic effects of uni- and biventricular pacing", *Am J Physiol Heart Circ Physiol*, vol. 285, (2003), H2788-H2796.

Yu, C.-M., et al., "High Prevalence of Left Ventricular Systolic and Diastolic Asynchrony in Patients With Congestive Heart Failure and Normal QRS Duration", *Heart*, vol. 89, (2003), 54-60.

"U.S. Appl. No. 11/264,941 Notice of Allowance mailed Feb. 20, 2008.", 13 pgs.

"U.S. Appl. No. 11/264,941, Notice of Allowance mailed Jun. 16, 2008", 10 pgs.

* cited by examiner

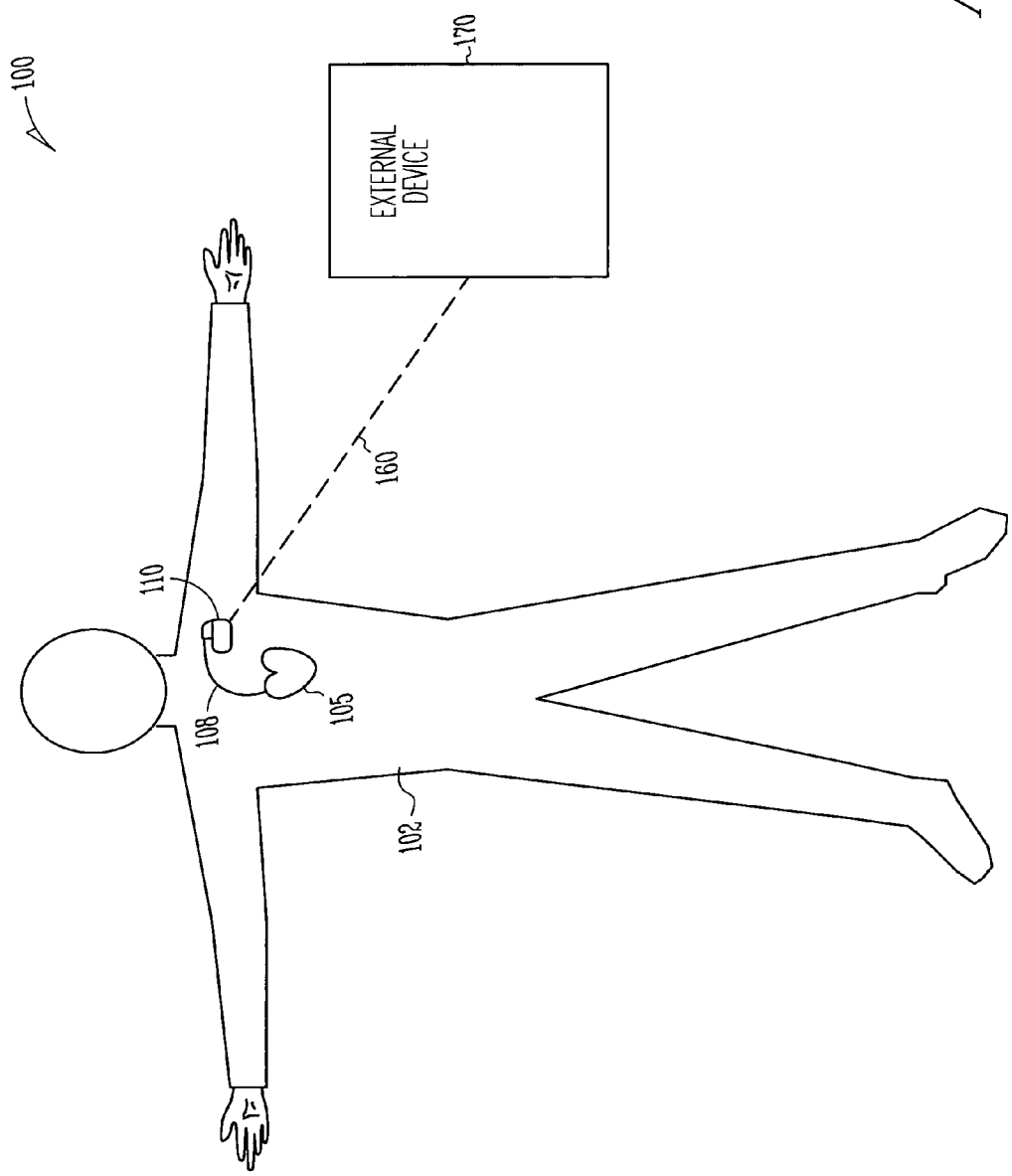

INTRACARDIAC IMPEDANCE AND ITS APPLICATIONS

TECHNICAL FIELD

The field generally relates to implantable medical devices and, in particular, but not by way of limitation, to systems and methods for detecting events related to cardiac activity.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect abnormally slow heart rate, or bradycardia. Additionally, the IMDs are able to detect abnormally rapid heart rate, or tachyarrhythmia. Although detecting an occurrence of tachyarrhythmia is important, it is more helpful if additional physiologic information is known about the arrhythmia, such as if the arrhythmia is hemodynamically stable or unstable. The IMDs are further able to detect differences in time between contractions of the left and right ventricles and to provide pacing therapy to resynchronize contractions of the left and right ventricles. However, proper resynchronization does not necessarily involve merely pacing the left and right ventricles simultaneously. Instead, there is a need to pace in a manner that improves the efficacy of the contractions. The present inventors have recognized a need for improved sensing of events related to cardiac activity.

SUMMARY

This document discusses, among other things, systems and methods for detecting events related to cardiac activity using measurements of intracardiac impedance. A system embodiment includes implantable electrodes and a medical device. The electrodes sense electrical signals of a heart of a subject. The medical device includes a cardiac signal sensing circuit coupled to the implantable electrodes, an impedance measurement circuit coupled to the same or different implantable electrodes, and a controller circuit coupled to the cardiac signal sensing circuit and the impedance measurement circuit. The cardiac signal sensing circuit provides a sensed cardiac signal. The impedance measurement circuit senses intracardiac impedance between the electrodes to obtain an intracardiac impedance signal. The controller circuit determines cardiac cycles of the subject using the sensed cardiac signal, and detects tachyarrhythmia using cardiac-cycle to cardiac-cycle changes in a plurality of intracardiac impedance parameters obtained from the intracardiac impedance signal.

A method embodiment includes sensing cardiac cycles of a patient, sensing intracardiac impedance to obtain an intracardiac impedance waveform, measuring a plurality of intracardiac impedance parameters from the waveform in correspondence with the cardiac cycles, and detecting tachyarrhythmia using at least one change in the plurality of intracardiac impedance parameters. The changes in the parameters are measured between multiple cardiac cycles.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

FIG. 1 illustrates an embodiment of portions of a system that uses an implantable medical device (IMD).

DETAILED DESCRIPTION

Figure 2A:
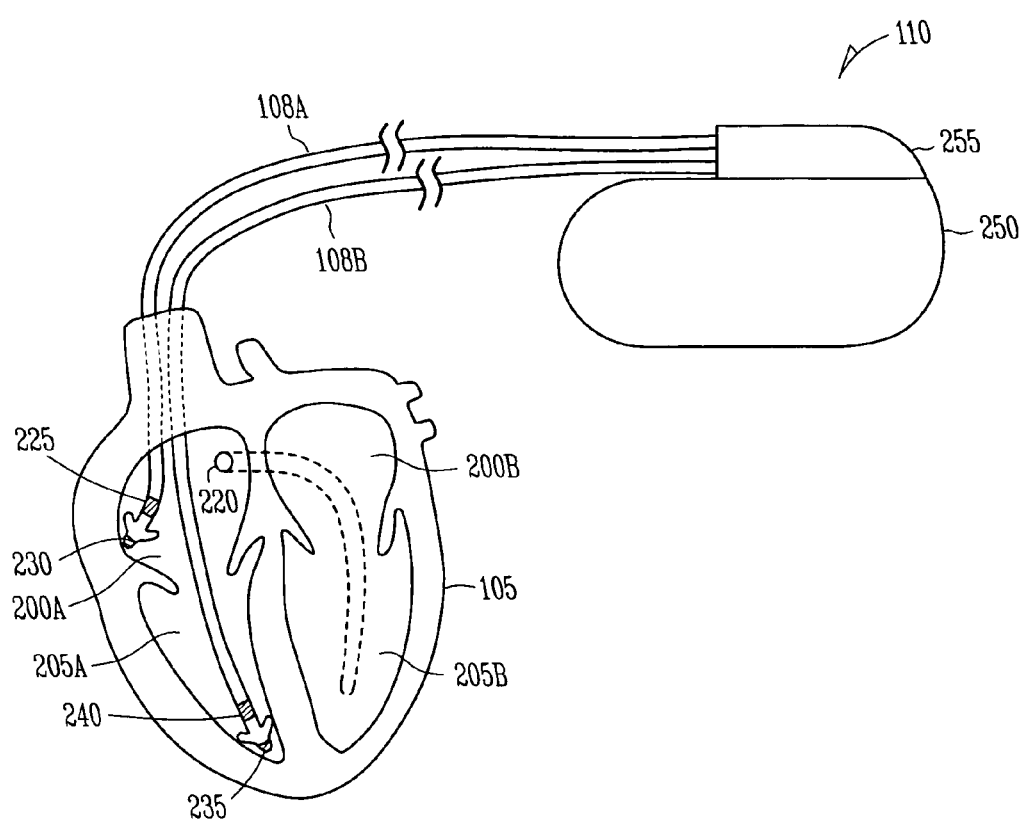
FIGS. 2A-B illustrate examples of an IMD coupled by one or more leads to a heart.

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses systems and methods for improved detection of cardiac events using measurements of intracardiac impedance, i.e., impedance measured within the heart. Monitoring intracardiac impedance provides physiologic information related to cardiac performance. For example, the volume of blood, V, in a heart chamber such as the left ventricle is linearly related to the inverse of the measured impedance of the heart chamber Z by the formula:

$$V = \frac{\rho L^2}{Z}, \quad (1)$$

where ρ is blood resistivity and L is the distance between impedance measuring electrodes. Volume varies inversely with impedance because electrolytes in the blood increase electrical conductivity. Thus, more blood results in lower measured impedance. Intracardiac impedance can also be used to monitor blood flow through the heart. The physiologic information obtained through monitoring intracardiac impedance can provide information related to the severity of an episode of tachycardia, a measure of hemodynamic response to heart failure therapy, and other changes to the hemodynamic system of a patient.

The intracardiac impedance is measured using a medical device. The impedance is measured between implantable electrodes placed in or near the heart chamber of interest. FIG. 1 illustrates an embodiment of portions of a system 100 that uses an implantable medical device (IMD) 110. As one example, the system 100 shown is used to treat a cardiac arrhythmia. The IMD 110 includes an electronics unit coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. Other examples include drug therapy devices such as drug pumps, neural stimulation devices, and ventricular assist devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end that is coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed in, near, or around a heart 105. The lead 108 or leads and electrodes may also typically be used for sensing electrical activity of the heart 105.

FIG. 2A illustrates an example of an IMD 110 coupled by one or more leads 108A-B to heart 105. Heart 105 includes a right atrium 200A, a left atrium 200B, a right ventricle 205A, a left ventricle 205B, and a coronary vein 220 extending from right atrium 200A. In the example, atrial lead 108A includes electrodes (electrical contacts, such as ring electrode 225 and tip electrode 230) disposed in, around, or near an atrium 200A of heart 105 for sensing signals, or delivering pacing therapy, or both, to the atrium 200A. Lead 108A optionally also includes additional electrodes, such as for delivering atrial cardioversion, atrial defibrillation, ventricular cardioversion, ventricular defibrillation, or combinations thereof to heart 105. Lead 108A optionally further includes additional electrodes for delivering pacing or resynchronization therapy to the heart 105.

Figure 2B:
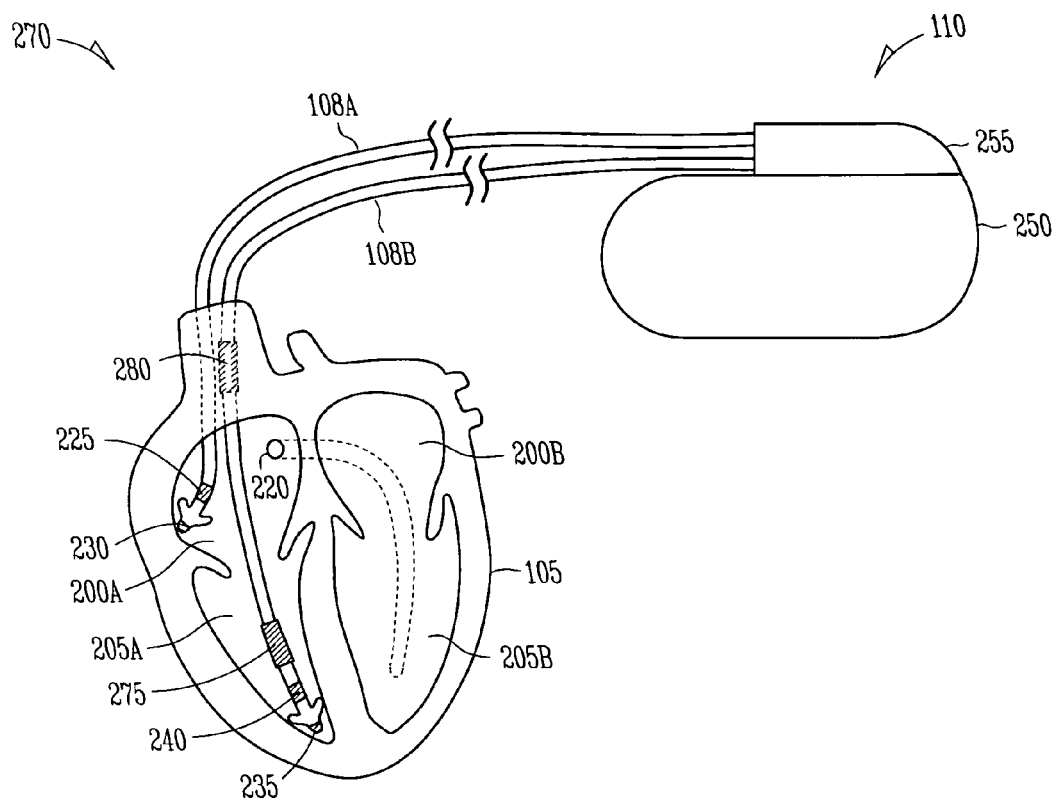

Ventricular lead 108B includes one or more electrodes, such as tip electrode 235 and ring electrode 240, for delivering sensing signals, for delivering pacing therapy, or for both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. For example, FIG. 2B shows a system 270 with lead 108B further including a first defibrillation coil electrode 275 located proximal to tip and ring electrodes 235, 240 for placement in a right ventricle, and a second defibrillation coil electrode 280 located proximal to the first defibrillation coil 275, tip electrode 235, and ring electrode 240 for placement in the superior vena cava. Other examples of leads 108A-B optionally further include additional electrodes for delivering pacing or resynchronization therapy to the heart 105.

Figure 3:
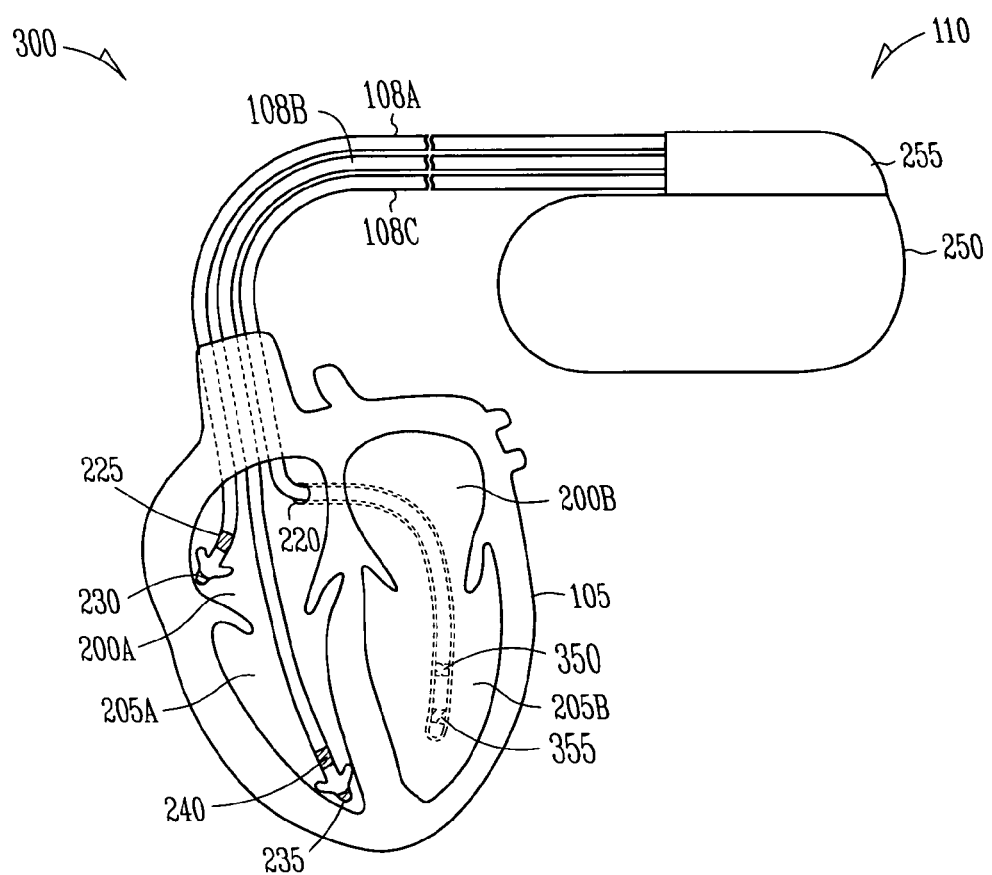
FIG. 3 illustrates another example of a system that uses an IMD.

Other forms of electrodes include meshes and patches which may be applied to portions of heart 105 or which may be implanted in other areas of the body to help "steer" electrical currents produced by IMD 110. In one embodiment, one of atrial lead 108A or ventricular lead 108B is omitted, i.e., a "single chamber" device is provided, rather than the dual chamber device illustrated in FIG. 2A. In another embodiment, additional leads are provided for coupling the IMD 110 to other heart chambers and/or other locations in the same heart chamber as one or more of leads 108A-B. The present methods and systems will work in a variety of configurations and with a variety of electrical contacts or "electrodes." FIG. 3 illustrates another example of a system 300 using an IMD 110. The system 300 includes a third cardiac lead 108C attached to the IMD 110 through the header 255. The third lead 108C includes ring electrodes 350 and 355 placed in the left ventricle 205B via the coronary vein 220. In another example, lead 108C includes electrodes for placement in the left atrium.

Sensing among different sets of electrodes often provides directional information regarding the propagation of cardiac signals and is often referred to as sensing among different vectors. For example, sensing from an electrode placed in or near the right atrium 200A to an electrode placed in or near the right ventricle 205A would be one vector, sensing from the right atrium 200A to the left atrium 200B would be a second vector, and sensing from the right ventricle 205A to a can electrode 250, or a header electrode 255, would be a third vector.

The medical device measures intracardiac impedance between implantable electrodes placed in or near the heart chamber of interest. As an example, the intracardiac impedance of the left ventricle 205B is measured between electrodes 355 and 350. In another example, the intracardiac impedance of the right ventricle 205A is measured between an electrode placed at the apex of the right ventricle 205A and an electrode placed in the right atrium 200A.

Figure 4:
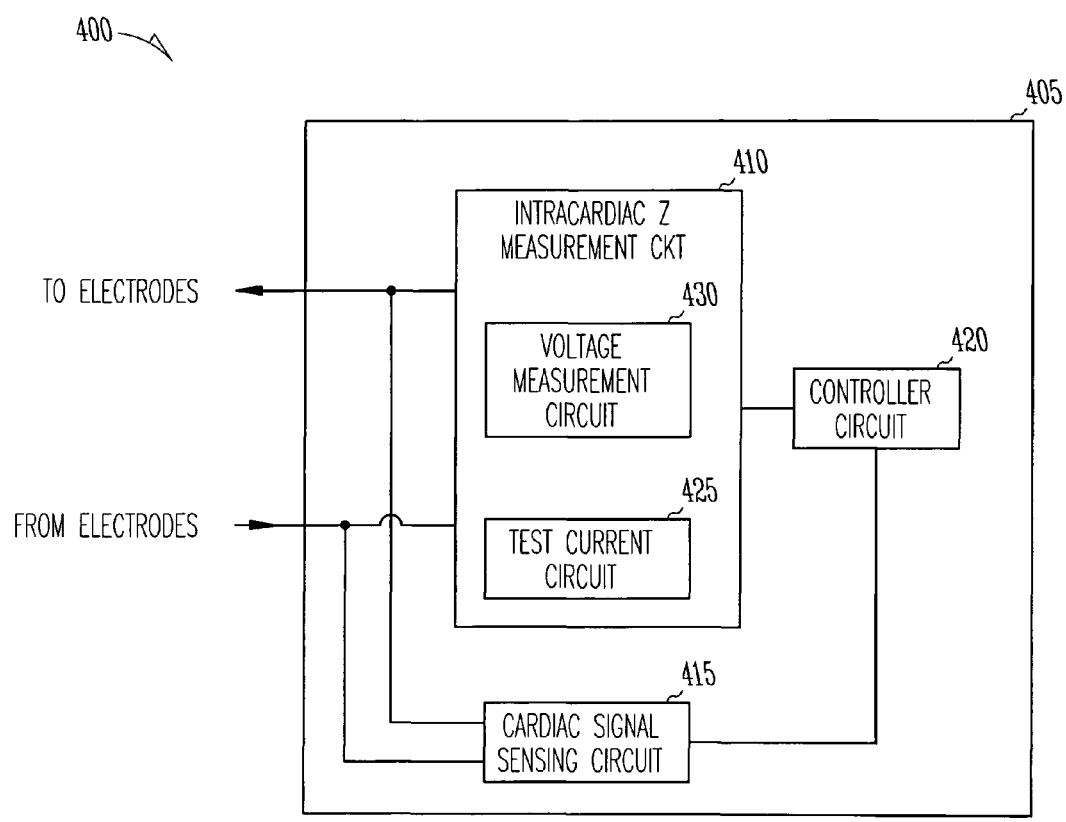
FIG. 4 shows a block diagram of an example of a system to monitor intracardiac impedance.

FIG. 4 shows a block diagram of an example of a system 400 to monitor intracardiac impedance. The system 400 includes a medical device 405. In some examples, the medical device 405 is implantable. The medical device 405 includes an intracardiac impedance measurement circuit 410, cardiac signal sensing circuit 415, and a controller circuit 420 coupled to the impedance measurement circuit 410 and cardiac signal sensing circuit 415. The intracardiac impedance measurement circuit 410 is coupled to implantable electrodes in order to obtain an intracardiac impedance signal between electrodes. In some examples, the intracardiac impedance measurement circuit 410 is coupled to a plurality of implantable electrodes and includes a test current circuit 425 and a voltage measurement circuit 430 coupled to the controller circuit 420. The test current circuit 425 delivers a specified test current using the implantable electrodes and the voltage measurement circuit 430 measures a voltage resulting from the test current. The resulting voltage may be measured using electrodes that are the same or different from the electrodes used to deliver the test current. For example, the test current could be delivered between ring electrodes on the leads of FIG. 2A, and the voltage could be measured using either the same ring electrodes or measured between the tip electrodes. To avoid unintended stimulation of the heart, the magnitude of the applied test current is small (e.g., 1-2 microamps) or the pulse width of the applied current is small (e.g., 1 milliamp amplitude, 15 microsecond pulse width, 47 millisecond period). This test current can be kept small enough to satisfy typical leakage current requirements of an implantable device. Similarly, a biphasic current waveform can be used to promote charge balance.

The cardiac signal sensing circuit 415 senses electrical cardiac signals associated with the action potential signals of a heart. The action potentials propagate through the heart's electrical conduction system to excite various regions of myocardial tissue. The sensing circuit 415 provides an electrical signal representative of such signals. Examples of cardiac signal sensing circuits 415 include, without limitation, a subcutaneous electrocardiogram (ECG) sensing circuit, an intracardiac electrogram (EGM) sensing circuit, and a wireless ECG sensing circuit. In a subcutaneous ECG sensing circuit, electrodes are implanted beneath the skin and the ECG signal obtained is referred to as subcutaneous ECG or far-field electrogram. In an intracardiac EGM circuit, at least one electrode is placed in or around the heart. A wireless ECG includes a plurality of electrodes to provide differential sensing of cardiac signals to approximate a surface ECG. Descriptions of wireless ECG systems are found in commonly assigned, co-pending U.S. patent application Ser. No. 10/795,126 by McCabe et al., entitled "Wireless ECG in Implantable Devices," filed on Mar. 5, 2004, which is incorporated herein by reference. The controller circuit 420 determines cardiac cycles using the cardiac signal sensing circuit 415 and measures cardiac-cycle to cardiac-cycle changes in a plurality of intracardiac impedance parameters, such as by being operable to perform an algorithm or algorithms implemented by hardware, software, firmware or any combination of hardware, software or firmware. Typically, intracardiac impedance is relatively stable under normal conditions. Monitoring intracardiac impedance for cycle-by-cycle changes detects potential changes to a patient's hemodynamic system in a relatively short period of time. Detecting changes quickly is import if the changes are due to heart failure (HF) decompensation or unstable tachycardias. In some examples, changes from one cardiac cycle to the next are measured. In some examples, changes are measured every third cardiac cycle. In some examples, changes are measured between a first cardiac cycle and a cardiac cycle that occurs several cycles later. This may be useful to save battery life by reducing the energy used for the measurements.

Figure 5A:
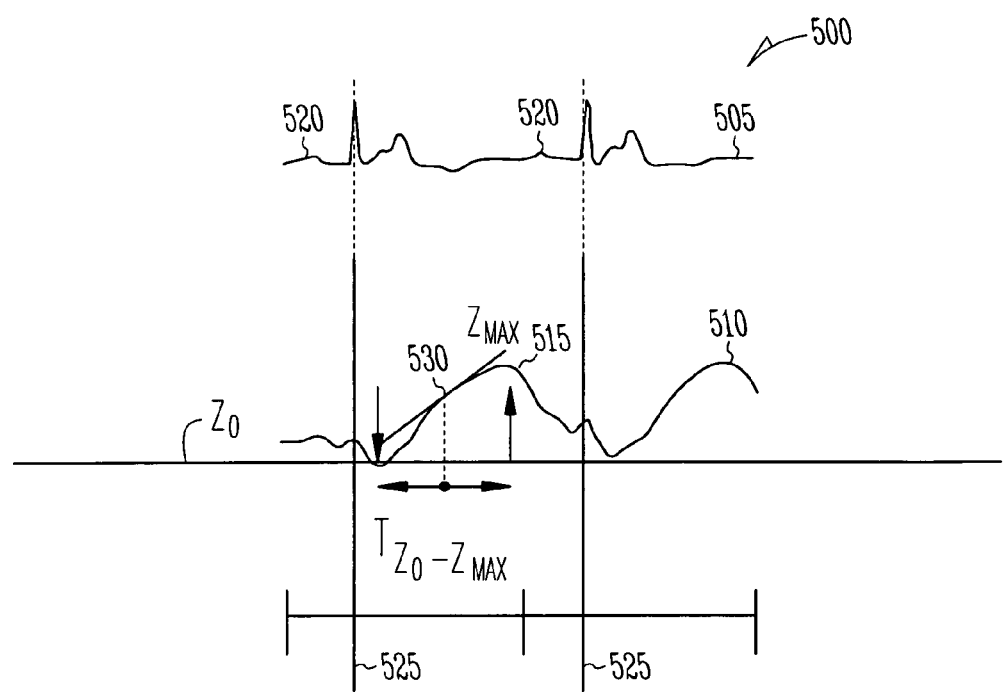
FIG. 5A illustrates graphs that include a measured cardiac signal waveform and a measured intracardiac impedance signal waveform.

FIG. 5A illustrates graphs 500 that include a measured cardiac signal waveform 505 and a measured intracardiac impedance waveform 510. The cardiac signal waveform 505 is an electrical waveform corresponding to action potentials of the ventricles of a heart. The graphs 500 show that the impedance waveform reaches a maximum value 515 just before a P-wave 520 corresponding to the ventricles beginning to fill with blood. The intracardiac impedance decreases to a minimum value until the ventricles begin to empty, at which point the impedance begins to increase. The segment of the impedance waveform 510 between the vertical bars 525 shows the intracardiac impedance variation over a cardiac cycle.

The controller circuit 420 of FIG. 4 derives many intracardiac impedance parameters from intracardiac impedance waveforms 510. One parameter shown in FIG. 5A is the baseline impedance value $Z_0$. $Z_0$ is a parameter that varies with a patient's heart size and depends on myocardial mass and blood volume. In one example, the baseline $Z_0$ is established at time of implant. In yet another example, the baseline $Z_0$ is established while a patient is in a predetermined physiologic state, such as at rest. In some examples, the controller circuit 420 of FIG. 4 includes an averaging circuit and establishes a baseline impedance value by-forming an ensemble or other average of minimum values of the waveform 510.

Another parameter shown in FIG. 5A is the maximum peak impedance value $Z_{max}$. This provides a measure of, among other things, a measure of the maximum change in size of a heart due to changing blood volume. Another parameter useful for measuring the volume of blood flowing through the heart is the area $Z_{area}$ between the impedance signal waveform 510 and the baseline $Z_0$. This measurement provides an approximation of the integral of the intracardiac impedance over the cardiac cycle. Another parameter shown in the Figure is the time interval of maximum impedance change $T_{Z0-Zmax}$, which is measured from the time when the sensed intracardiac impedance signal waveform exceeds the measured baseline intracardiac impedance value to the time it reaches the maximum intracardiac impedance value. This provides a measure of heart contraction speed. Yet another parameter shown is the slope of the intracardiac impedance wave form measured at $\frac{1}{2}T_{Z0-Zmax}$ 530, or $S_{1/2TZ0-Zmax}$. The time interval and the slope of the waveform provide a measure of the efficacy of heart contractions. The slope and area under the curve measurements ($Z_{area}$) are comprehensive parameters which use the relatively simple parameters $Z_0$ and $Z_{max}$ to calculate cardiac performance.

Figure 5B:
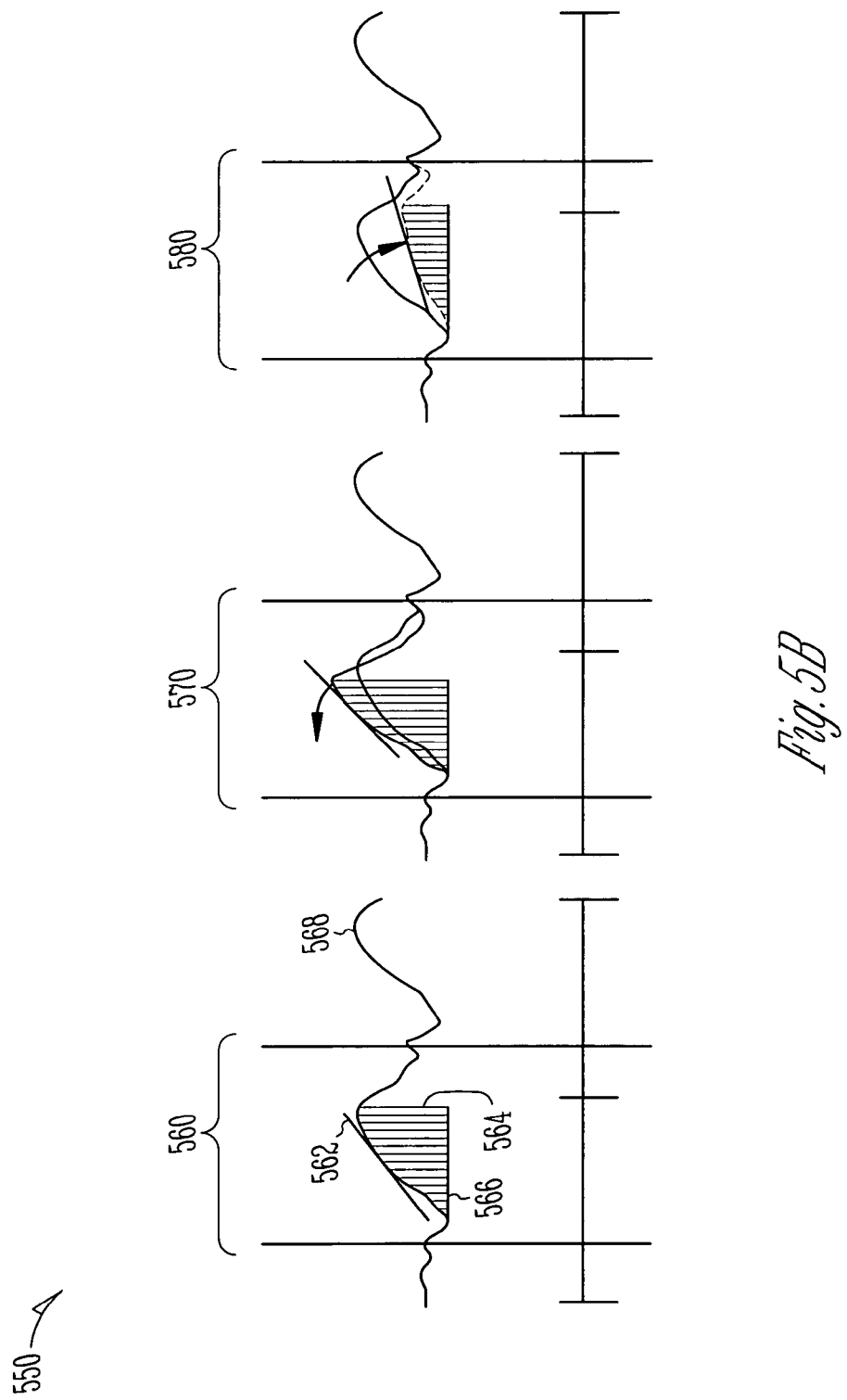
FIG. 5B shows a set of graphs of measured intracardiac impedance waveforms.

The controller circuit 420 of FIG. 4 uses measured changes in the intracardiac impedance parameters to detect or verify tachyarrhythmia in a patient. In some examples, the controller circuit 420 detects tachyarrhythmia from a sudden decrease in cardiac performance manifested as a change in the intracardiac impedance parameters. FIG. 5B shows a set of graphs 550 of measured intracardiac impedance waveforms. Graph 560 illustrates a slope 562 of the waveform and an area 564 above a baseline intracardiac impedance value 566 and below an intracardiac impedance wave form 568. Graph 570 illustrates a change in intracardiac impedance that increases the slope of the waveform and the area under the waveform and above the baseline value. Because intracardiac impedance is inversely proportional to volume, the change may indicate an increase in the change in volume of blood filling the ventricles and being emptied from the ventricles during a cardiac cycle. Graph 580 illustrates a change that decreases the slope, and thus may indicate that the volume of blood flow is not changing to the same degree as in graphs 560 and 570, possibly because the ventricles are not emptying properly. If the difference between the baseline value $Z_0$ and the maximum value $Z_{max}$ rapidly decreases over cardiac cycles, this may be an indication that the tachyarrhythmia is ventricular fibrillation or ventricular tachycardia.

In some examples, the controller circuit 420 detects tachyarrhythmia from a combination of a variation in heart rate and a change in the intracardiac impedance parameters. A rate detected tachyarrhythmia, such as tachycardia, together with a decrease in cardiac performance indicated by changes in intracardiac impedance parameters, may indicate that the tachycardia is unstable. In some examples, unstable tachycardia is indicated from a significant reduction in the intracardiac impedance curve, such as shown between the cardiac cycles in graphs 560 and 580 of FIG. 5B, during tachycardia. A rate detected tachycardia together without a decrease in cardiac performance indicated by changes in intracardiac impedance parameters may indicate the tachycardia is stable.

In some examples, the medical device 405 includes a therapy circuit to deliver a therapy to a patient. In some examples, the therapy circuit is coupled to the electrodes to provide pacing and/or defibrillation energy in conjunction with the electrodes disposed in or near a heart. The electrodes are used along with sense amplifiers for sensing electrical activity of a heart. In some examples, the medical device 405 is a neural stimulation device and the therapy circuit is coupled to the electrodes to provide energy for neural stimulation, such as a vagal nerve stimulation device. In some examples, the therapy circuit initiates delivery of a drug therapy, such as from a drug reservoir or from a drug patch of an iontophoretic device.

In some examples, the medical device 405 is capable of delivering more than one type of therapy and the measured changes in intracardiac impedance parameters are used to determine the type of therapy to provide to a patient. For example, if the controller circuit 420 determines that the tachyarrhythmia is ventricular tachycardia and the intracardiac impedance parameters indicate that the tachycardia is stable, the controller circuit 420 first attempts to terminate the tachycardia using anti-tachycardia pacing (ATP) before providing high-energy shock therapy. If the controller circuit 420 determines that the tachyarrhythmia is ventricular tachycardia and the intracardiac impedance parameters indicate that the tachycardia is unstable, the controller circuit 420 immediately attempts to terminate the tachycardia using high-energy shock therapy.

Figure 6:
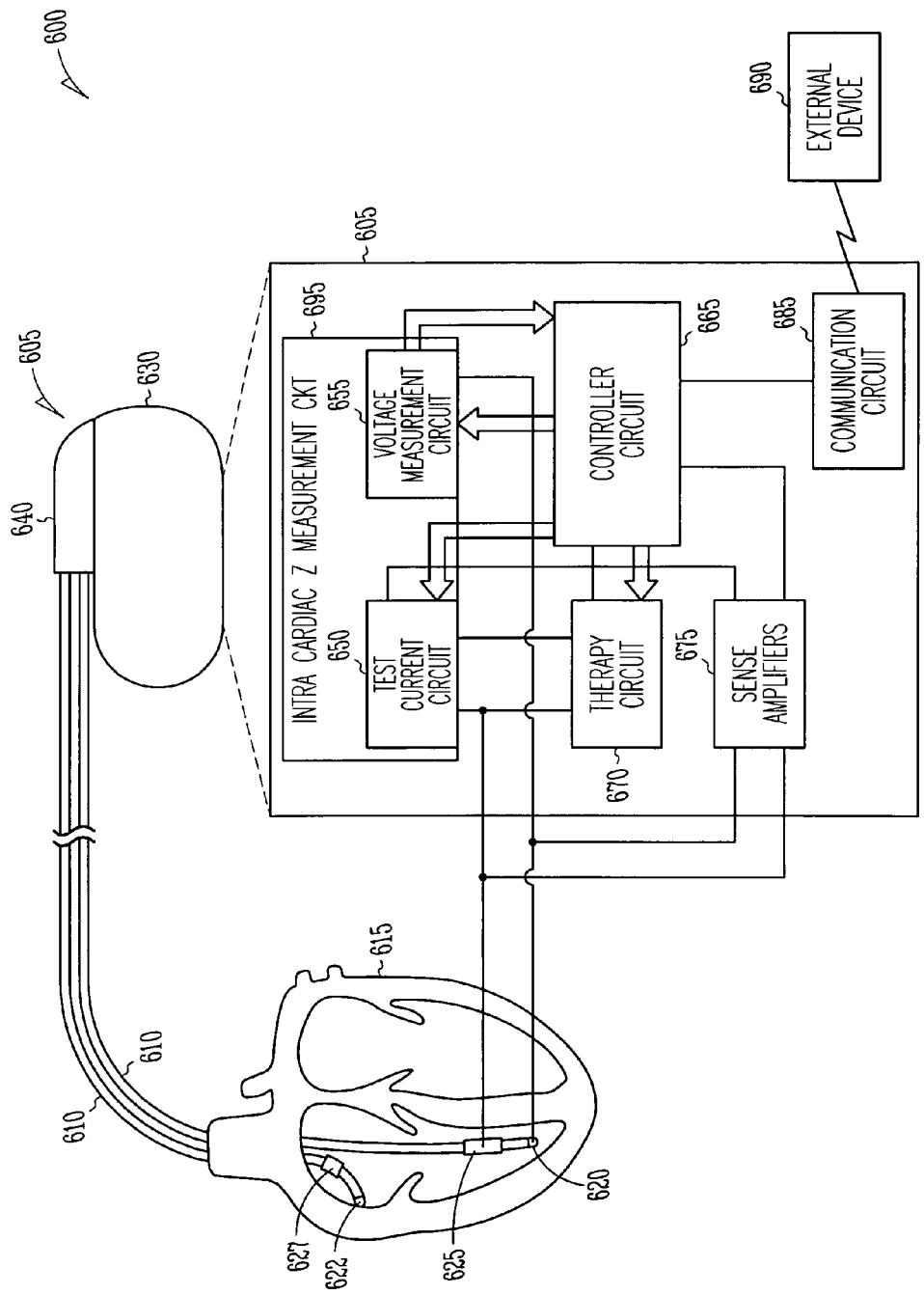
FIG. 6 is an illustration of portions of another example of a system to monitor intracardiac impedance.

FIG. 6 is an illustration of portions of another example of a system 600 to monitor intracardiac impedance. In this example, the system 600 includes an IMD 605 that is a cardiac rhythm management device. The IMD 605 is coupled to heart 615 by cardiac leads 610 that include lead tip and ring electrodes 620, 622, 625, 627. The cardiac leads 610 are connected to the IMD at header 640. The IMD 605 includes components that are enclosed in a hermetically-sealed canister or "can" 630. A therapy circuit 670 is used to provide cardiac function management therapy such as pacing and/or defibrillation energy in conjunction with the electrodes disposed in or around heart 615. The leads 610 and lead electrodes 620, 622, 625, 627 are used in conjunction with sense amplifiers 675 for sensing electrical activity of a heart 615.

The IMD 605 includes an intracardiac impedance measurement circuit 695 coupled to a controller circuit 665. The impedance measurement circuit 695 includes a test current circuit 650 and a voltage measurement circuit 655. As an example, the test current is delivered between the right atrium and the right ventricle using ring electrodes 625 and 627. To determine the intracardiac impedance, the resulting voltage is measured using tip electrodes 620 and 622. Any combination of electrodes can be used to deliver the current and measure the voltage. For example, the electrodes used in FIG. 6 to deliver the test current and those to measure the test voltage could be swapped. Alternatively, some or all of the electrodes used to deliver the current could be the same as the electrodes to measure the voltage. For example, the test current could be delivered from the ring electrode 625 to ring electrode 627 and the voltage could be measured from the tip electrode 620 to ring electrode 627.

In some examples, the medical device 605 further includes a memory circuit coupled to the controller circuit 665. The memory circuit stores intracardiac impedance parameters measured by the controller circuit 665. In some examples, the controller circuit 665 detects tachyarrhythmia using changes in the measured and stored parameters. For example, a decrease in cardiac performance may be indicated by an increase in either the baseline impedance value $Z_0$, the maximum peak impedance value $Z_{max}$, or both $Z_0$ and $Z_{max}$. In some examples, the controller circuit 665 detects tachyarrhythmia using a combination of heart rate and changes in the measured and stored parameters.

In some examples, the memory circuit stores trends in the measured intracardiac impedance signal parameters. Trending of data helps to establish a timeframe over which the change occurred. The timeframe can provide clues as to the cause of the change or changes. For example, changes due to an acute myocardial infarction are immediate and in hemodynamic changes within seconds or minutes. In contrast, hemodynamic changes due to worsening HF are gradual and occur over hours or days.

According to some examples, the system 600 further includes an external device 690 operable to communicate with the IMD 605 using the communication circuit 685. The communication is through wireless signals such as telemetry signals or RF signals. In some examples, the external device 690 is part of, or in communication with, a computer network such as a hospital computer network or the internet. In some examples, the external device 690 is part of, or in communication with, a communication network. The medical device 605 communicates wirelessly with the external device 690 and the medical device 605 communicates the trend data to the external device 690. In some examples, the external device 690 includes a display to display the trend data.

According to some examples, the system 600 includes electrodes for placement in or around chambers on both the left side and right of the heart 615, such as the lead configuration of FIG. 3, and the IMD 605 provides cardiac resynchronization therapy (CRT) to heart 615. The controller circuit 665 adjusts one or more parameters related to CRT based on measured changes in the intracardiac impedance parameters. As an illustrative example, if a measured value of maximum peak impedance value $Z_{max}$ is low, the controller circuit 665 adjusts the offset between pacing of the right ventricle and pacing of the left ventricle to increase the difference between the baseline impedance value $Z_0$ and the maximum peak impedance value $Z_{max}$. In another example, the controller circuit 665 adjusts the offset between pacing of the right ventricle and pacing of the left ventricle to increase both $Z_{max}$ and the slope of the intracardiac impedance waveform. In some examples, the parameter related to CRT is adjusted using an external device after trending of the measured intracardiac parameters is reviewed using the external device.

Figure 7:
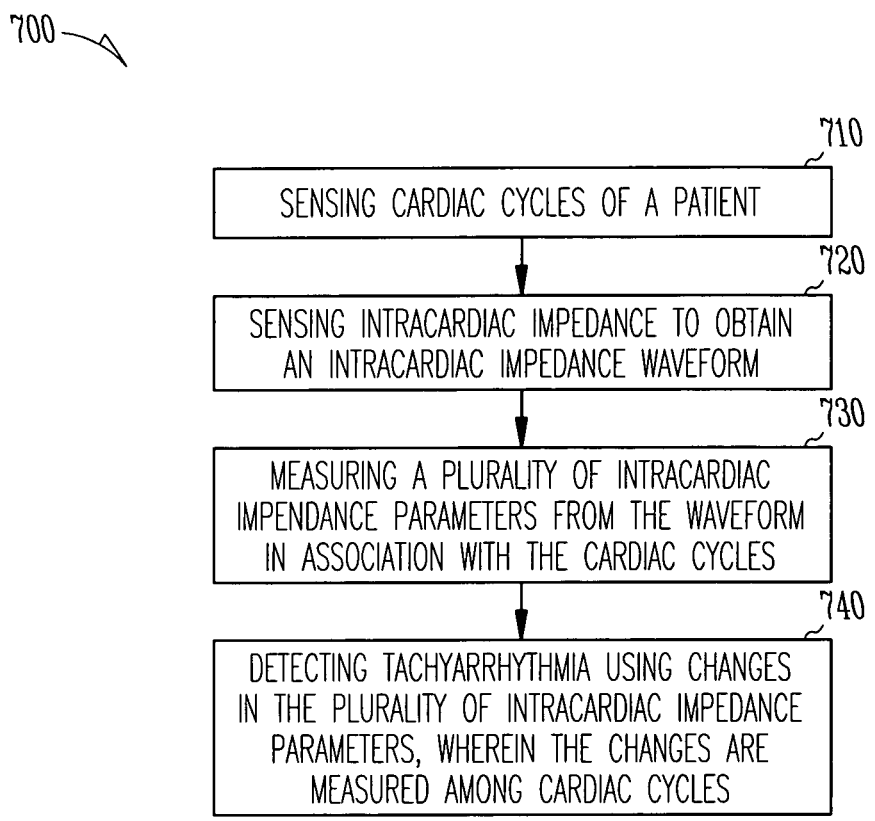
FIG. 7 shows a block diagram of an example of a method for detecting cardiac events using measurements of intracardiac impedance.

FIG. 7 shows a block diagram of an example of a method 700 for detecting cardiac events using measurements of intracardiac impedance. At 710, cardiac cycles of a patient are sensed by monitoring the patient's electrical cardiac signals. In some examples, the cardiac signals are sensed using a subcutaneous electrocardiogram (ECG) sensing circuit, or an intracardiac electrogram (EGM) sensing circuit, or a wireless ECG sensing circuit. At 720, intracardiac impedance is sensed to obtain an intracardiac impedance waveform. In some method examples, the cardiac cycles and intracardiac impedance are sensed using an IMD. At 730, a plurality of intracardiac impedance parameters is measured from the sensed waveform in association with the cardiac cycles. This provides monitoring of the intracardiac impedance parameters on a cardiac-cycle by cardiac-cycle basis. In some examples, the plurality of intracardiac impedance parameters includes a baseline intracardiac impedance value $Z_0$. The baseline value may be established by forming an ensemble or other average of multiple sampled values of the waveform. In some examples, the plurality of intracardiac impedance parameters includes an area between a sensed intracardiac impedance signal waveform and the measured intracardiac impedance baseline value. This measurement approximates an integral over the cardiac cycle of the intracardiac impedance greater than the baseline value.

In some examples, the plurality of intracardiac impedance parameters includes measuring a maximum intracardiac impedance value $Z_{max}$ during a cardiac cycle. In some examples, the plurality of intracardiac impedance parameters includes measuring a time interval beginning when a sensed intracardiac impedance signal waveform exceeds the measured baseline intracardiac impedance value and ending when the waveform reaches the maximum intracardiac impedance value. In some examples, the plurality of intracardiac impedance parameters includes measuring a slope of the intracardiac impedance waveform. In some of the examples, the slope is measured at the midpoint of the time interval that it takes the intracardiac impedance signal to reach the maximum value from the baseline value.

At 740, detecting tachyarrhythmia is detected using the changes in the plurality of intracardiac impedance parameters measured among the cardiac cycles. In some examples, tachyarrhythmia is detected using the changes in the intracardiac impedance parameters alone. For example, if the difference between the baseline value $Z_0$ and the maximum value $Z_{max}$ rapidly decreases over cardiac cycles, this may be an indication that the tachyarrhythmia is ventricular fibrillation or ventricular tachycardia. In some examples, tachyarrhythmia is detected using the changes in the intracardiac impedance parameters together with variations in heart rate.

Figure 8:
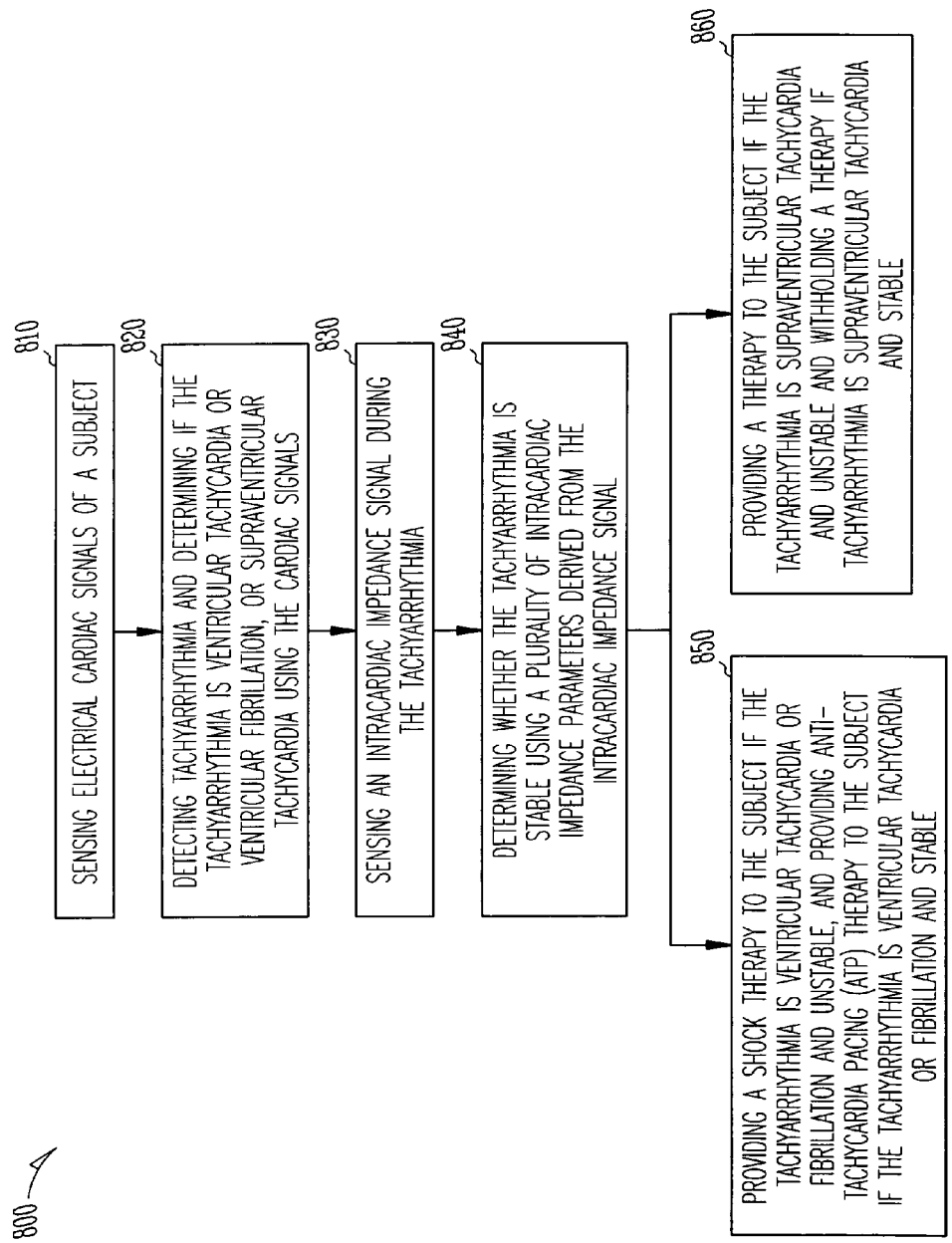
FIG. 8 shows another block diagram of an example of a method for detecting cardiac events using intracardiac impedance measurements.

FIG. 8 shows another block diagram of an example of a method 800 for detecting cardiac events using intracardiac impedance measurements. At 810, electrical cardiac signals of a subject are sensed. At 820, tachyarrhythmia is detected. It is then determined whether the tachyarrhythmia is ventricular tachycardia or ventricular fibrillation, or supraventricular tachycardia using the cardiac signals. In some examples, tachyarrhythmia is detected from heart rate, such as by a sudden onset of a number of fast beats. Whether a tachyarrhythmia is ventricular tachycardia or ventricular fibrillation, or supraventricular tachycardia is then determined using the morphology of sensed cardiac signals. Systems and methods to detect tachyarrhythmia and to discriminate ventricular tachycardia or ventricular fibrillation from supraventricular tachycardia are described in Hsu et al., U.S. Pat. No. 6,275,732, entitled "Multiple Stage Morphology Based System Detecting Ventricular Tachycardia and Supraventricular Tachycardia," which is incorporated herein by reference. At 830, an intracardiac impedance signal is sensed during the tachyarrhythmia. In some embodiments the cardiac signals and the impedance signal are sensed using an IMD.

At 840, it is determined whether the tachyarrhythmia is stable using a plurality of intracardiac impedance parameters derived from the intracardiac impedance signal. In some examples, the plurality of intracardiac impedance parameters are measured in association with cardiac cycles determined from the cardiac signals. At 850, shock therapy is provided to the subject if the tachyarrhythmia is ventricular tachycardia or fibrillation and unstable, and providing anti-tachycardia pacing (ATP) therapy to the subject if the tachyarrhythmia is ventricular tachycardia or fibrillation and stable. In some examples, ATP therapy is first provided to the patient and shock therapy is resorted to if ATP does not mitigate the tachyarrhythmia. Some examples of the method 800 further include, at 860, providing a therapy to the subject if the tachyarrhythmia is supraventricular tachycardia and unstable and withholding a therapy if tachyarrhythmia is supraventricular tachycardia and stable.

Figure 9:
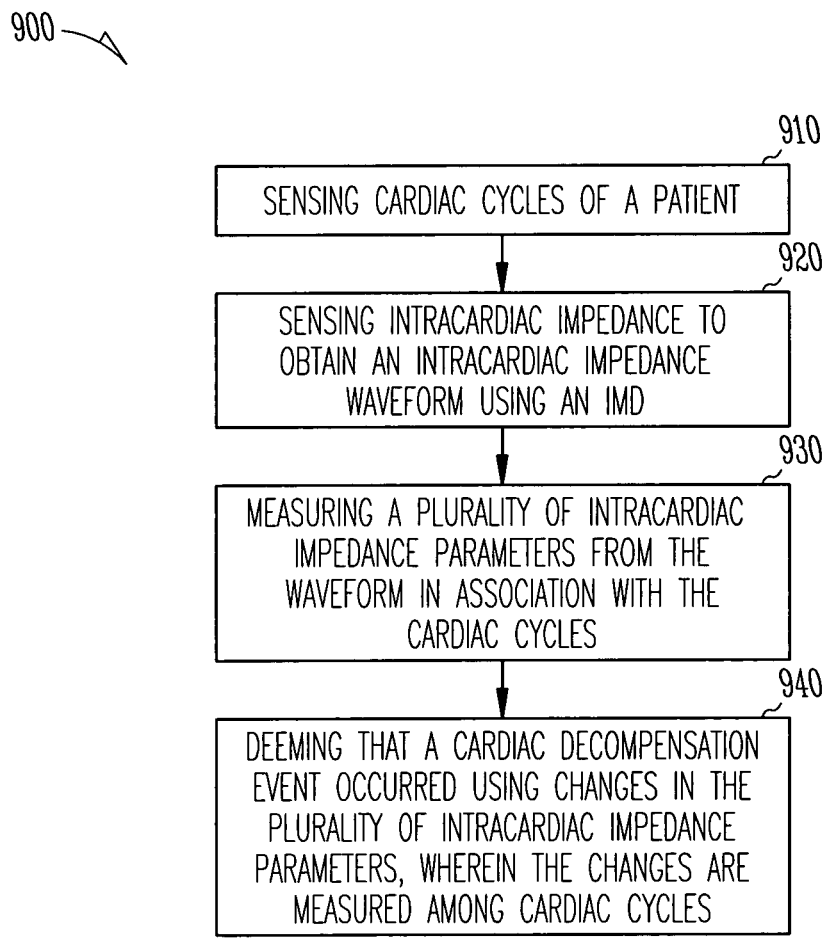
FIG. 9 shows another block diagram of an example of a method for detecting cardiac events using intracardiac impedance measurements.

FIG. 9 shows another block diagram of an example of a method 900 for detecting cardiac events using intracardiac impedance measurements. At 910, the cardiac cycles of a patient are sensed using any of the methods discussed previously. At 920, intracardiac impedance is sensed using an IMD to obtain an intracardiac impedance waveform. At 930, a plurality of intracardiac impedance parameters is measured from the waveform in association with the cardiac cycles. In some examples, the plurality of intracardiac impedance parameters includes a baseline impedance value $Z_0$. In some examples, the plurality of intracardiac impedance parameters includes the maximum peak impedance value $Z_{max}$. In some examples, the plurality of intracardiac impedance parameters includes the area $Z_{area}$ between the impedance signal waveform and the baseline value $Z_0$. In some examples, the plurality of intracardiac impedance parameters includes the time interval of maximum impedance change, $T_{Z0-Zmax}$, measured from the time when the sensed intracardiac impedance signal waveform exceeds the measured baseline intracardiac impedance value to the time it reaches the maximum intracardiac impedance value. In some examples, the plurality of intracardiac impedance parameters includes the slope of the intracardiac impedance waveform measured at one-half the time interval from when the waveform exceeds a baseline impedance value to when it reaches a maximum impedance value.

The measured parameters are monitored are monitored for changes on a cardiac-cycle by cardiac-cycle basis. At 940, a cardiac decompensation event is deemed to have occurred using changes in the plurality of measured intracardiac impedance parameters. In some embodiments, detecting cardiac decompensation includes detecting a decrease in cardiac performance in the absence of tachycardia using at least one intracardiac impedance parameter. Returning to FIG. 5B, graph 580 shows a decreasing change in intracardiac impedance during cardiac cycles. The decreasing change would be manifested in several of the mentioned intracardiac impedance parameters. For example, the change in $Z_{max}$ between cardiac cycles would be decreasing, the slope of the intracardiac impedance waveform would be decreasing, and the area between the waveform and the baseline value $Z_0$ would be decreasing. If the changes occur while the heart rate remains constant or stable, it may be an indication that the change occurred without an intervening episode of tachycardia and the change may indicate HF decompensation.

In some examples, because hemodynamic changes due to worsening HF are gradual and occur over hours or days, trending of the parameters may be used to monitor the changes. In some examples, changes in the parameters that occur among cardiac cycles, such as from one cardiac cycle to the next, are trended. In some examples, the IMD detects the decompensation event and sets an indication of the decompensation. The indication may be communicated to an external device to alert a caregiver. In some examples, the trending information is transmitted to an external device and the external device detects the decompensation event. In some examples, a therapy provided to the patient by the IMD is adjusted based at least in part on the cardiac decompensation event.

If the intracardiac impedance trending information includes a decrease in cardiac performance to a low level (such as a decrease in contraction strength manifested as the decrease in impedance illustrated in graph 580 of FIG. 5B) and the low level is maintained for a prolonged period of time in spite of medical intervention, this trending information may indicate that remodeling of the heart has occurred. In some method examples, such changes can be monitored and detected by trending intracardiac impedance parameters. For example, if the trending shows that a patient experienced a temporary increase in cardiac performance followed by a decrease in cardiac performance without any evidence of tachycardia, the trending deems that heart remodeling has occurred. In some examples, at least one therapy parameter of the IMD is adjusted in accordance with the trending.

The systems and methods discussed herein show that monitoring intracardiac impedance enhances detection of cardiac events such as tachycardia, and enhance monitoring and adjusting of, among other things, cardiac rhythm management systems. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   a medical device including:
      a cardiac cycle sensing circuit, the sensing circuit configured to provide a sensed cardiac cycle;
      an impedance measurement circuit configured to provide an intracardiac impedance signal; and
      a controller circuit coupled to the impedance measurement circuit, the controller circuit configured to detect tachyarrhythmia from the intracardiac impedance signal using at least two of:
      a cardiac-cycle-to-cardiac-cycle change in a value of a baseline intracardiac impedance value calculated, for a particular cardiac cycle, to represent the baseline intracardiac impedance for that particular cardiac cycle;
      a cardiac-cycle-to-cardiac-cycle change in a value of maximum intracardiac impedance value calculated, for a particular cardiac cycle, to represent the maximum intracardiac impedance for that particular cardiac cycle; and
      a cardiac-cycle-to-cardiac-cycle change in a slope value of the intracardiac impedance waveform signal, for a particular cardiac cycle, the slope value measured at a time corresponding to one-half of a time interval over which a maximum intracardiac impedance change occurs during that particular cardiac cycle.

2. The system of claim 1, wherein the controller circuit is configured to detect tachyarrhythmia using at least one of:
   a cardiac-cycle-to-cardiac-cycle change in an area between the intracardiac impedance signal waveform and the baseline intracardiac impedance value, wherein the area is calculated, for a particular cardiac cycle, to represent the area corresponding to that particular cardiac cycle; and
   a cardiac-cycle-to-cardiac-cycle change in a time interval of maximum intracardiac impedance change, wherein the time interval is calculated, for a particular cardiac cycle, to represent the time interval corresponding to that particular cardiac cycle.

3. The system of claim 1, wherein the medical device includes a memory circuit to store intracardiac impedance parameters measured in accordance with at least one cardiac cycle, and wherein the controller circuit is further operable to detect tachyarrhythmia using a change from stored intracardiac impedance parameters and measured intracardiac impedance parameters.

4. The system of claim 3, wherein the medical device is configured to store at least one trend for at least one intracardiac impedance parameter.

5. The system of claim 1, wherein the medical device is implantable and further includes a communication circuit to communicate at least one trend for at least one intracardiac impedance parameter to an external device, and wherein the external device is in communication with a communication network.

6. The system of claim 5, wherein the external device includes a display, and wherein the external device is further operable to display intracardiac impedance information.

7. The system of claim 1, wherein the medical device includes a therapy circuit coupled to the controller circuit, wherein the controller circuit is operable to initiate a therapy upon detection of tachyarrhythmia.

8. The system of claim 7, further including at least one electrical lead comprising implantable electrodes, and wherein the implantable electrodes includes at least one coil shock electrode located distally to other electrodes on the lead, the coil shock electrode adaptable for placement in a right ventricle of a heart.

9. The system of claim 7, further including at least one electrical lead comprising implantable electrodes, and wherein the implantable electrodes includes at least one coil shock electrode located proximally to other electrodes on the lead, the coil shock electrode adaptable for placement in a superior vena cava.

10. The system of claim 1, comprising implantable electrodes, and wherein the implantable electrodes includes at least one electrode adaptable for placement in a left atrium of the heart.

11. The system of claim 1, comprising implantable electrodes, and wherein the implantable electrodes includes at least one electrode adaptable for placement in a left ventricle of the heart.

12. A method comprising:
sensing cardiac cycles of a patient;
sensing intracardiac impedance to obtain an intracardiac impedance waveform;
measuring intracardiac impedance parameters from the waveform including at least two of:
   a cardiac-cycle-to-cardiac-cycle change in a value of a baseline intracardiac impedance value calculated, for a particular cardiac cycle, to represent the baseline intracardiac impedance for that particular cardiac cycle;
   a cardiac-cycle-to-cardiac-cycle change in a value of maximum intracardiac impedance value calculated, for a particular cardiac cycle, to represent the maximum intracardiac impedance value for that particular cardiac cycle; and
   a cardiac-cycle-to-cardiac-cycle change in a slope value of an intracardiac impedance waveform signal, for a particular cardiac cycle, the slope value measured at a time corresponding to one-half of a time interval over which a maximum intracardiac impedance change occurs during the particular cardiac cycle; and
detecting tachyarrhythmia using at least one change in the intracardiac impedance parameters.

13. The method of claim 12, wherein measuring intracardiac impedance parameters includes measuring, for a particular cardiac cycle, a cardiac-cycle-to-cardiac-cycle change in a value of an area between the sensed intracardiac impedance signal waveform and the baseline intracardiac impedance value, wherein the change in area value is measured to represent the area value corresponding to the particular cardiac cycle.

14. The method of claim 12, wherein measuring intracardiac impedance parameters includes measuring, for a particular cardiac cycle, a cardiac-cycle-to-cardiac-cycle change in a time interval from when a sensed intracardiac impedance signal waveform exceeds the measured baseline intracardiac impedance value to the time it reaches the maximum intracardiac impedance value, wherein the change in the time interval is measured to represent the time interval value for that particular cardiac cycle.

15. The method of claim 12, wherein sensing cardiac cycles and sensing intracardiac impedance includes sensing cardiac cycles and intracardiac impedance using an implantable medical device (IMD).

16. A method comprising:
sensing electrical cardiac signals of a subject;
detecting tachyarrhythmia and determining whether the tachyarrhythmia is ventricular tachycardia or ventricular fibrillation, or supraventricular tachycardia using the electrical cardiac signals;
sensing an intracardiac impedance signal during the tachyarrhythmia;
determining whether the tachyarrhythmia is stable using intracardiac impedance parameters derived from the intracardiac impedance signal wherein the intracardiac impedance parameters include at least two of:
   a cardiac-cycle-to-cardiac-cycle change in a value of a baseline intracardiac impedance value calculated, for a particular cardiac cycle, to represent the baseline intracardiac impedance for that particular cardiac cycle;
   a cardiac-cycle-to-cardiac-cycle change in a value of maximum intracardiac impedance value calculated, for a particular cardiac cycle, to represent the maximum intracardiac impedance for that particular cardiac cycle; and
   a cardiac-cycle-to-cardiac-cycle change in a value of a slope of the intracardiac impedance waveform signal, for a particular cardiac cycle, the slope value measured at a time corresponding to one-half of a time interval over which a maximum intracardiac impedance change occurs during that particular cardiac cycle; and
providing a shock therapy to the subject if the tachyarrhythmia is ventricular tachycardia or fibrillation and is unstable, and providing anti-tachycardia pacing (ATP) therapy to the subject if the tachyarrhythmia is ventricular tachycardia or fibrillation and is stable.

17. The method of 16, wherein providing ATP therapy to the subject if the tachyarrhythmia is ventricular tachycardia or fibrillation and stable includes providing ATP therapy before resorting to shock therapy if ATP does not mitigate the tachyarrhythmia.

18. The method of claim 16, further including providing a therapy to the subject if the tachyarrhythmia is supraventricular tachycardia and unstable and withholding a therapy if tachyarrhythmia is supraventricular tachycardia and stable.

19. The method of 16, wherein determining whether the tachyarrhythmia is stable using the intracardiac impedance signal includes measuring the intracardiac impedance parameters from a sensed intracardiac impedance signal waveform in association with cardiac cycles.

20. The method of 16, wherein sensing the electrical cardiac signals and sensing the intracardiac impedance signal includes sensing using an IMD, and wherein providing a shock therapy includes providing shock therapy using an IMD.

21. A method comprising:
sensing cardiac cycles of a patient;
sensing intracardiac impedance using an IMD to obtain an intracardiac impedance waveform;
measuring intracardiac impedance parameters from the waveform including at least two of:
   a cardiac-cycle-to-cardiac-cycle change in a value of a baseline intracardiac impedance value calculated, for a particular cardiac cycle, to represent the baseline intracardiac impedance for that particular cardiac cycle;
   a cardiac-cycle-to-cardiac-cycle change in a value of maximum intracardiac impedance value calculated, for a particular cardiac cycle, to represent the maximum intracardiac impedance for that particular cardiac cycle; and
   a cardiac-cycle-to-cardiac-cycle change in a value of a slope of the intracardiac impedance waveform signal, for a particular cardiac cycle, the slope value measured at a time corresponding to one-half of a time interval over which a maximum intracardiac impedance change occurs during the particular cardiac cycle; and deeming that a cardiac decompensation event occurred using at least one change in the intracardiac impedance parameters.

22. The method of claim 21, wherein the method further includes monitoring heart rate of the patient to detect tachycardia, and wherein deeming that a cardiac decompensation event occurred includes detecting a decrease in cardiac performance in the absence of tachycardia using the change in the intracardiac impedance parameters measured between multiple cardiac cycles.

23. The method of claim 22, wherein measuring intracardiac impedance parameters includes measuring, for a particular cardiac cycle, a cardiac-cycle-to-cardiac-cycle change in an area between the intracardiac impedance waveform and a baseline impedance value, wherein the measured area value represents the area corresponding to that particular cardiac cycle, and wherein detecting a decrease in cardiac performance includes detecting a decrease in the measured area.

24. The method of claim 22, wherein measuring intracardiac impedance parameters includes measuring, for a particular cardiac cycle, a cardiac-cycle-to-cardiac-cycle change in a time interval of maximum intracardiac impedance change measured to represent the time interval for that particular cardiac cycle, and wherein detecting a decrease in cardiac performance includes detecting an increase in the measured time interval.

25. The method of claim 21, further including adjusting a therapy provided to the patient by the IMD based at least in part on an occurrence of cardiac decompensation.

26. A method comprising:
sensing cardiac cycles of a patient using an implantable medical device (IMD);
sensing intracardiac impedance using the IMD to obtain an intracardiac impedance waveform;
measuring intracardiac impedance parameters from the waveform including at least two of:
a cardiac-cycle-to-cardiac-cycle change in a value of a baseline intracardiac impedance value calculated, for a particular cardiac cycle, to represent the baseline intracardiac impedance for that particular cardiac cycle;
a cardiac-cycle-to-cardiac-cycle change in a value of maximum intracardiac impedance value calculated, for a particular cardiac cycle, to represent the maximum intracardiac impedance for that particular cardiac cycle; and
a cardiac-cycle-to-cardiac-cycle change in a value of a slope of the intracardiac impedance waveform signal, for a particular cardiac cycle, the slope value measured at a time corresponding to one-half of a time interval over which a maximum intracardiac impedance change occurs during the particular cardiac cycle; and
trending changes in the plurality of intracardiac impedance parameters, wherein the changes are measured between multiple cardiac cycles.

27. The method of claim 26, wherein the method further includes changing at least one therapy parameter of the IMD according to the trending.

28. The method of claim 26, wherein the method further includes deeming that cardiac remodeling has occurred according to the trending.

* * * * *